(12) United States Patent (10) Patent No.: US 9,339,691 B2
Brammer (45) Date of Patent: May 17, 2016

(54) SYSTEM AND METHOD FOR CONTROLLING AN EXERCISE DEVICE

(71) Applicant: ICON Health & Fitness, Inc., Logan, UT (US)

(72) Inventor: Chase Brammer, Providence, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 33 days.

(21) Appl. No.: 13/734,970

(22) Filed: Jan. 5, 2013

(65) Prior Publication Data

US 2013/0178337 A1 Jul. 11, 2013

Related U.S. Application Data

(60) Provisional application No. 61/583,524, filed on Jan. 5, 2012.

(51) Int. Cl.
*A63B 71/00* (2006.01)
*A63B 24/00* (2006.01)
*A63B 15/02* (2006.01)
*A63B 71/06* (2006.01)
*G06F 19/00* (2011.01)
*A63B 21/22* (2006.01)
*A63B 22/00* (2006.01)
(Continued)

(52) U.S. Cl.
CPC ......... *A63B 24/0075* (2013.01); *A63B 24/0087* (2013.01); *A63B 71/0622* (2013.01); *G06F 19/3481* (2013.01); *A63B 21/225* (2013.01); *A63B 22/0023* (2013.01); *A63B 22/0056* (2013.01); *A63B 22/0076* (2013.01); *A63B 22/0235* (2013.01); *A63B 22/0242* (2013.01); *A63B 22/0605* (2013.01); *A63B 22/0664* (2013.01); *A63B 2022/002* (2013.01); *A63B 2024/009* (2013.01); *A63B 2071/068* (2013.01); *A63B 2071/0638* (2013.01); *A63B 2071/0644* (2013.01); *A63B 2225/20* (2013.01); *A63B 2225/50* (2013.01); *A63B 2230/062* (2013.01); *A63B 2230/30* (2013.01); *A63B 2230/75* (2013.01)

(58) Field of Classification Search
USPC ..................................... 482/1, 8–9
See application file for complete search history.

(56) References Cited

U.S. PATENT DOCUMENTS

| | | |
|---|---|---|
| 6,053,844 A | 4/2000 | Clem |
| 6,193,631 B1 | 2/2001 | Hickman |
| 7,645,213 B2 | 1/2010 | Watterson et al. |

(Continued)

*Primary Examiner* — Loan H Thanh
*Assistant Examiner* — Shila Jalalzadeh Abyan
(74) *Attorney, Agent, or Firm* — Holland & Hart LLP

(57) ABSTRACT

In general, the present invention relates to exercise devices and systems that can receive and run workout programs that include control command subsets that control the moveable members of a plurality of different exercise devices. Exercise devices of the present invention are able to ignore the control command subset(s) that do not control their moveable member(s) and recognize the control command subset(s) that control their moveable member(s). Exercise devices of the present invention are further able to, if necessary, perform a sizing restriction to the relevant control command subset(s). Motivational content may also be modified in connection with or independently from a sizing restriction made to the control commands. The present invention also relates to a method for controlling one or more exercise device with a workout file that includes control command subsets that control the moveable members of a plurality of different exercise devices.

17 Claims, 9 Drawing Sheets

(51) Int. Cl.
*A63B 22/02* (2006.01)
*A63B 22/06* (2006.01)

(56) References Cited

U.S. PATENT DOCUMENTS

| | | | |
|---|---|---|---|
| 8,103,517 B2 | 1/2012 | Hinnebusch | |
| 2004/0077462 A1* | 4/2004 | Brown | A63B 24/0006 482/8 |
| 2004/0127335 A1* | 7/2004 | Watterson | A63B 21/005 482/8 |
| 2005/0233861 A1* | 10/2005 | Hickman | A63B 24/0084 482/8 |
| 2007/0033069 A1* | 2/2007 | Rao | A63B 24/00 705/2 |
| 2007/0265138 A1* | 11/2007 | Ashby | A63B 22/02 482/8 |
| 2008/0207401 A1* | 8/2008 | Harding | A63B 24/0006 482/4 |
| 2009/0163321 A1* | 6/2009 | Watterson | A63B 22/00 482/4 |
| 2010/0035726 A1* | 2/2010 | Fisher | A63B 24/0084 482/8 |
| 2011/0015039 A1* | 1/2011 | Shea | 482/5 |
| 2012/0179772 A1 | 7/2012 | Hinnebusch | |

* cited by examiner

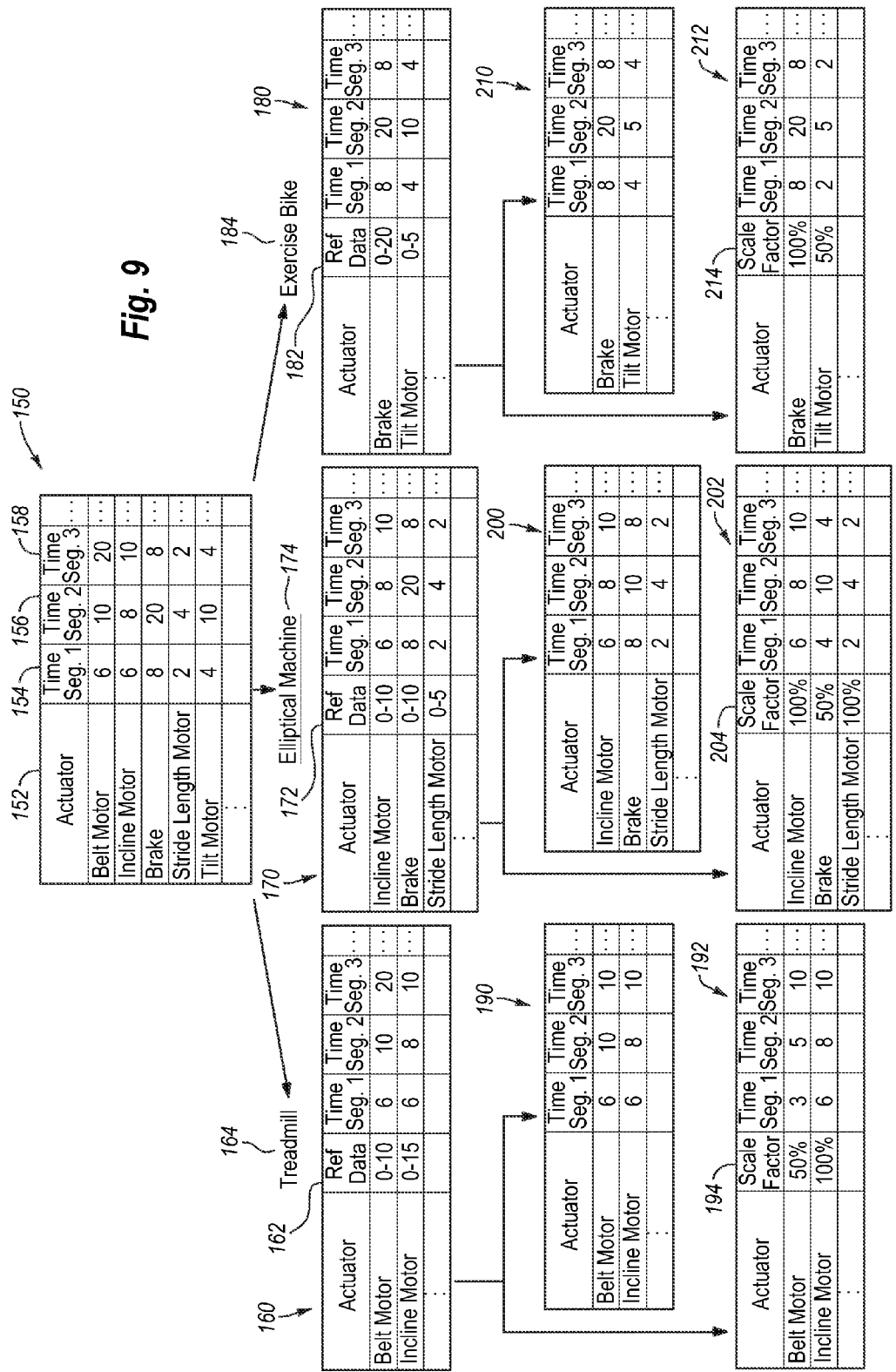

SYSTEM AND METHOD FOR CONTROLLING AN EXERCISE DEVICE

CROSS-REFERENCE TO RELATED APPLICATIONS

This application claims priority to U.S. Provisional Patent Application No. 61/583,524 filed Jan. 5, 2012.

TECHNICAL FIELD

In general, the present invention relates to exercise equipment. More specifically, the present invention relates to methods, systems, and devices for providing workout files that are compatible with a plurality of different exercise devices.

BACKGROUND

Stationary exercise devices have become an increasingly popular way to exercise. To combat the boredom that is often experienced by individuals that exercise with these devices, stationary exercise devices are often sold with a number of different workout files that are saved within the electronics of the device. These workout files may include a "fat burn" workout, a "hills" workout and/or other workout files. Limited memory space however, restricts the number of different workout files that can be saved within the electronics of the exercise device.

Efforts have been made to increase the number of workout files available on stationary exercise devices. For example, U.S. Pat. No. 7,645,213, U.S. Pat. No. 6,193,631, and U.S. Pat. No. 6,053,844 relate to various ways of providing additional workout files or control commands to exercise devices. Due to the differences in exercise devices, however, workout files have to this point been specifically tailored for each exercise device. In other words, workout files that control moveable members and/or actuators in one type of exercise device may not control moveable members and/or actuators in another type of exercise device. Further, a workout file that is compatible with one exercise device may not be compatible with other exercise devices in the same class. This may be due to the fact that the operating parameter range on one exercise device is different from the operating parameter range on another exercise device. For example, a workout file that is compatible with a treadmill having a deck that is inclinable to a twenty percent grade may not be compatible with a treadmill whose deck is only inclinable to a fifteen percent grade.

SUMMARY OF THE INVENTION

In one aspect of the disclosure, an exercise device includes a moveable member having one or more operating parameters that are selectively adjustable within a limited range and one or more actuators that selectively adjust the one or more selectively adjustable operating parameters within the limited range.

In another aspect that may be combined with any of the aspects herein, the exercise device has a receiving port that receives workout files.

In another aspect of the invention that may be combined with any of the aspects herein, the workout files have a first control command subset that provides instructions for controlling the one or more actuators that selectively adjust the operating parameters of the moveable member.

In another aspect that may be combined with any of the aspects herein, the workout files have a second control command subset that does not provide instructions for controlling the one or more actuators that selectively adjust the operating parameters of the moveable member.

In another aspect that may be combined with any of the aspects herein, the exercise device has a processing unit that is in communication with the one or more actuators and the receiving port.

In another aspect that may be combined with any of the aspects herein, the processing unit includes reference data that enables the processing unit to select the first control command subset from the workout file.

In another aspect that may be combined with any of the aspects herein, the reference data enables the processing unit to analyze the first control command subset and, if necessary, apply a sizing restriction to the first control command subset creating a restricted control command subset, such that the restricted control command subset provides instructions for controlling the one or more actuators that selectively adjust the operating parameters of the moveable member within the limited range.

In another aspect that may be combined with any of the aspects herein, the sizing restriction applied by the processing unit is a scaling sizing restriction.

In another aspect that may be combined with any of the aspects herein, the sizing restriction applied by the processing unit is a capping sizing restriction.

In another aspect that may be combined with any of the aspects herein, the workout file further includes motivational content.

In another aspect that may be combined with any of the aspects herein, the motivational content is synchronized with or reflective of the control commands within a workout file.

In another aspect that may be combined with any of the aspects herein, the reference data enables the processing unit to modify the motivational content.

In another aspect that may be combined with any of the aspects herein, the motivational content includes a video of terrain to be traversed during performance of an exercise In another aspect that may be combined with any of the aspects herein, the processing unit modifies the horizon line on the video so that the horizon line on the video remains synchronized with the restricted control command subset.

In another aspect that may be combined with any of the aspects herein, the processing unit modifies the playback speed of the video so that the playback speed of the video remains synchronized with the restricted control command subset.

In another aspect that may be combined with any of the aspects herein, the motivational content includes a graphical representation of a workout file profile.

In another aspect that may be combined with any of the aspects herein, the processing unit modifies the graphical representation of the workout file profile so that the workout file profile remains reflective of the restricted control command subset.

In another aspect that may be combined with any of the aspects herein, the motivational content includes projected biological metrics In another aspect that may be combined with any of the aspects herein, the processing unit modifies the projected biological metrics so that the projected biological metrics remain reflective of the restricted control command subset.

In another aspect that may be combined with any of the aspects herein, the workout file is a universal workout file and includes control command subsets for at least two different types of exercise devices.

In another aspect that may be combined with any of the aspects herein, the first subset of control commands may be modified by the processing unit based on user input.

In another aspect that may be combined with any of the aspects herein, the receiving port is a memory device drive.

In another aspect that may be combined with any of the aspects herein, a remote computer makes available at least one workout file that includes a first subset of control commands and a second subset of control commands.

In another aspect that may be combined with any of the aspects herein, a first exercise device has a first processing unit and one or more operating parameters that are selectively adjustable within a limited range, based on the first subset of control commands from the workout file.

In another aspect that may be combined with any of the aspects herein, the first processing unit includes reference data that allows the first exercise device to identify and execute the first subset of control commands.

In another aspect that may be combined with any of the aspects herein, a second exercise device has a second processing unit and one or more operating parameters that are selectively adjustable within a limited range based on the second subset of control commands from the workout file.

In another aspect that may be combined with any of the aspects herein, the second processing unit includes reference data that allows the second exercise device to identify and execute the second subset of control commands.

In another aspect that may be combined with any of the aspects herein, a method for controlling one or more exercise devices includes providing a workout file having a plurality of control command subsets, including a first subset of control commands and a second subset of control commands.

In another aspect that may be combined with any of the aspects herein, the method further includes providing an exercise device that has a processing unit and a first moveable member that is selectively adjustable within a limited range and that is adjustable based on the first subset of control commands.

In another aspect that may be combined with any of the aspects herein, the method further includes selecting the first subset of control commands from the plurality of control command subsets.

In another aspect that may be combined with any of the aspects herein, the method further includes adjusting the first moveable member based on the first subset of control commands.

In another aspect that may be combined with any of the aspects herein, the method further includes applying a sizing restriction to the first subset of control commands such that the control commands adjust the moveable member within the limited range.

In another aspect that may be combined with any of the aspects herein, the method further includes providing a second exercise device having a processing unit and a second moveable member that is selectively adjustable within a limited range and that is adjustable based on the second subset of control commands.

In another aspect that may be combined with any of the aspects herein, the method further includes adjusting the second moveable member based on the second subset of control commands.

DESCRIPTION OF THE DRAWINGS

FIG. 9 illustrates tables arranged in a schematic representation of an implementation of the present invention.

DETAILED DESCRIPTION

The present invention provides methods, systems, and devices for providing workout files that are compatible with a plurality of different exercise devices. Exercise devices of the present invention are able to identify control commands within the workout file that are compatible with the exercise device. Exercise devices of the present invention may also apply a sizing restriction to the compatible control commands within the workout file such that the control commands adjust operating parameters of the exercise device within a limited range.

Figure 1:
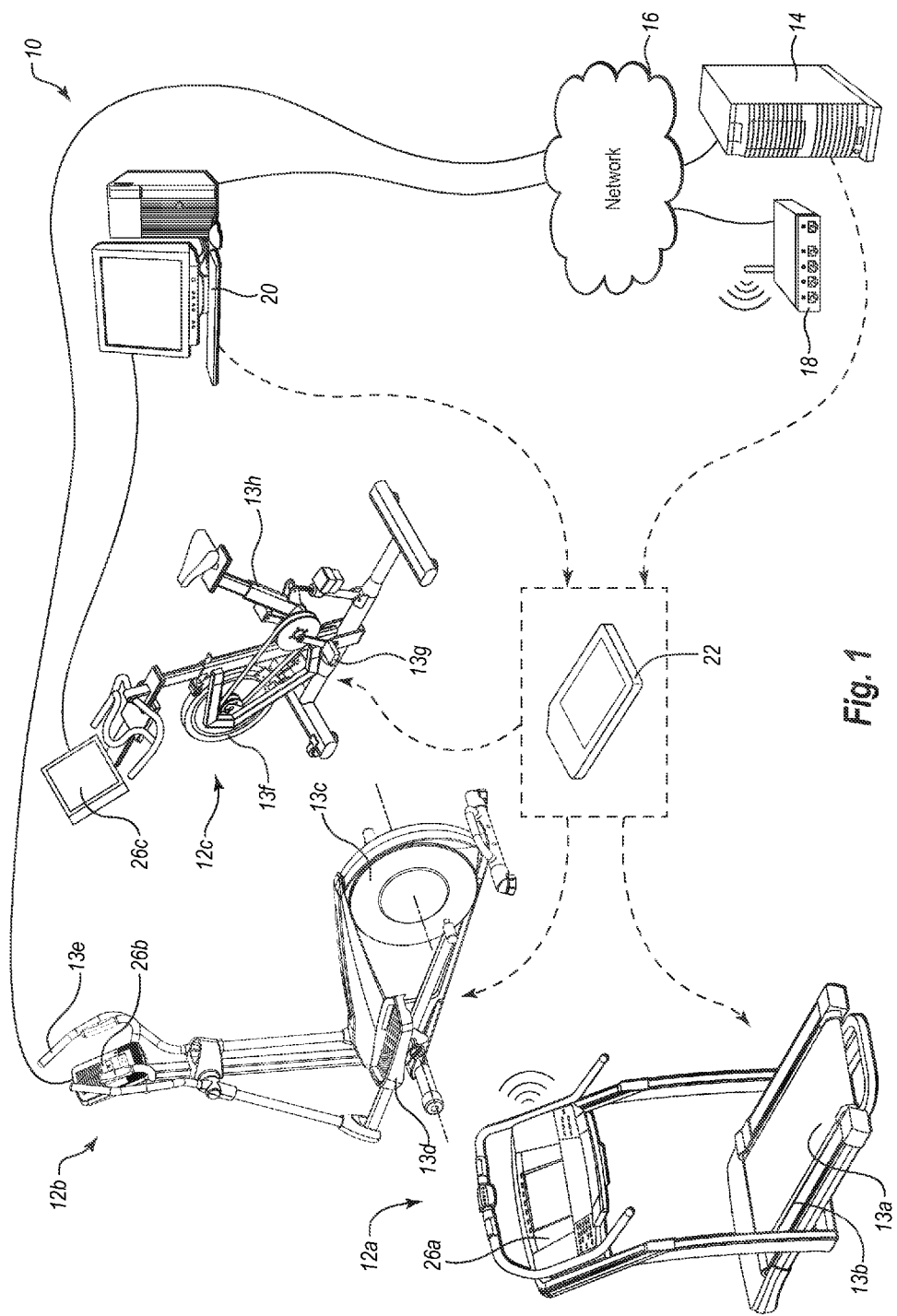
FIG. 1 illustrates an exercise system according to one embodiment of the present invention.

FIG. 1 illustrates an exercise system 10. Exercise system 10 includes exercise devices 12a-c, which have moveable members 13a-h, which move during performance of an exercise. Moveable members 13a-h have operating parameters that are selectively adjustable within a limited range. One or more actuators may selectively adjust the operating parameters of moveable members 13a-h within the limited range. Exercise devices 12a-c also include one or more receiving ports (see FIG. 2). Specifically, exercise devices 12a-c include wired connection ports, wireless connection ports, memory device drives, CD drives, DVD drives, disk drives, etc. Exercise devices 12a-c are capable of receiving data through these receiving ports.

Data received by exercise devices 12a-c through their receiving port(s) can include workout files. Workout files can comprise in whole or in part exercise programming, which may include control commands and motivational content. As described in more detail hereafter, control commands may provide instructions for adjusting the operating parameters (such as the speed, incline, difficulty level, time, distance, and the like) of a moveable member. Motivational content broadly refers to any video or visual material either alone or in combination with audio material, including dialog, narration, sound effects, and/or music. Control commands may or may not be synchronized with motivational content.

Exercise device 12a is illustrated as a treadmill. Exercise device 12a may include multiple different moveable members including a belt 13a and a deck 13b. Moveable members 13a-b include one or more operating parameters that are selectively adjustable within a limited range. One example of an operating parameter on exercise device 12a is the speed of belt 13a. Belt 13a may rotate at different speeds within a limited range. An actuator (see FIG. 2), for example a belt motor, may selectively adjust the speed at which belt 13a rotates within the limited range. Another example of an operating parameter on exercise device 12a is the inclination of deck 13b. Deck 13b may be selectively inclinable to different angles within a limited range. An actuator, for example an incline motor, may selectively adjust the incline of deck 13b within the limited range.

Exercise device 12b is illustrated as an elliptical machine. Exercise device 12b may include multiple different moveable members including a flywheel 13c, foot rails 13d, and arm rails 13e. During performance of an exercise on exercise device 12b, movement of foot rails 13d and arm rails 13e cause flywheel 13c to rotate. Moveable members 13c-e include one or more operating parameters that are selectively adjustable within a limited range. One example of an operating parameter on exercise device 12b is the amount of resistance applied to flywheel 13c. A differing amount of resistance can be applied to flywheel 13c to make the movement of foot rails 13d and arm rails 13e more or less difficult. An actuator, such as a brake, may be used to selectively adjust the amount of resistance that is applied to flywheel 13c. Another example of an operating parameter on exercise device 12b is the inclination of foot rails 13d. Foot rails 13d may be inclinable to different angles within a limited range. An actuator, such as an incline motor, may selectively adjust the incline of foot rails 13d within the limited range. Yet another example of an operating parameter on exercise device 12b is the stride length of foot rails 13d or arm rails 13e. The stride length of the foot rails 13d and/or arm rails 13e may be adjustable to different distances within a limited range. An actuator, for example a stride length motor, may selectively adjust the stride length of the foot rails 13d or arm rails 13e within the limited range.

Exercise device 12c is illustrated as an exercise bike. Exercise device 12c may include multiple different moveable members including a flywheel 13f, pedals 13g, and a frame 13h. During performance of an exercise on exercise device 12c, movement of pedals 13g cause flywheel 13f to rotate. These moveable members include one or more operating parameters that are selectively adjustable within a limited range. One example of an operating parameter on exercise device 12c is the amount of resistance applied to flywheel 13f. A differing amount of resistance can be applied to flywheel 13f to make rotation of the pedals 13g more or less difficult. An actuator, such as a brake, may be used to selectively adjust the amount of resistance that is applied to flywheel 13f within the limited range. Another example of an operating parameter on exercise device 12c is the configuration of frame 13h. Frame 13h may tilt forward, backward, or from side to side within a limited range. An actuator, such as tilt motor, may selectively adjust frame 13h within the limited range.

A communication system 14 (e.g., a remote computer or website) can provide data, including workout files, to exercise devices 12a-c through a network 16 or a portable memory device 22. Network 16, may be a local area network (LAN), wide area network (WAN), wireless network, packetized network, real-time network, and the like. Network 16 facilitates communication between exercise devices 12a-12c and communication system 14.

Connection between exercise devices 12a-12c and network 16 can be made via a variety of different communication line connections. For example, exercise device 12a is illustrated with a wireless receiving port and is capable of wireless communication with communication system 14 via network 16 through a wireless router 18. The wireless receiving port may also be receptive to communications via broadcast technology, including television broadcast over the airwaves, satellite, the Internet, DSL, G-Lite, infra-red (IR) technology, other high-speed data connections, or any other suitable wireless transmission technology or medium. Exercise device 12b includes a wired receiving port. Specifically, exercise device 12b is shown with a direct hardwire connection to network 16. Exercise device 12c also includes a wired receiving port. Specifically, exercise bike 12b is shown with a hardware connection to personal computer 20, which has a hardware connection with network 16. Thus, system 10 may allow for any type of connection between an exercise device 12 and network 16, whether wired or wireless.

Although each of the elements of system 10 are shown separated one from another, it may be appreciated by one skilled in the art that the hardware and/or software elements of the present invention may be incorporated within two or more elements. For example, personal computer 20 may be incorporated within exercise device 12a, exercise device 12b, or exercise device 12c.

A receiving port on any of exercise devices 12a-c could also be a memory device drive such as a USB port or a SD card drive. For example, exercise devices 12a-12c may each include a portable memory device drive that receives and is able to read portable memory device 22. Portable memory device 22 can receive workout files from communication system 14 via network 16 and personal computer 20. Alternatively, Portable memory device 22 can receive workout files directly from communication system 14.

Figure 2:
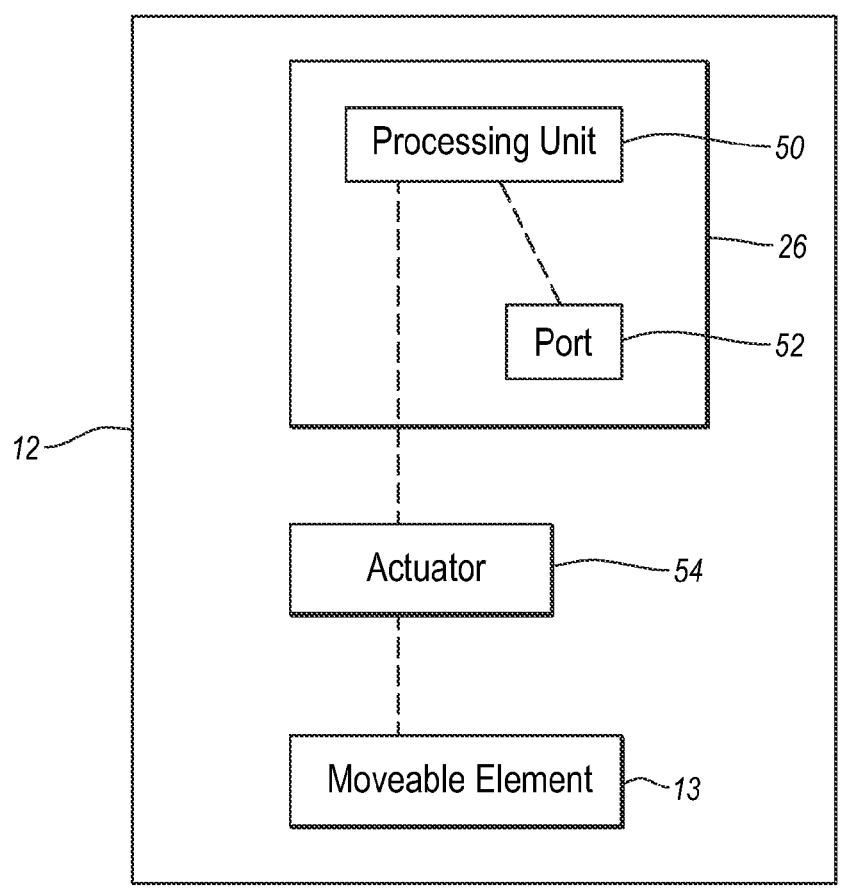
FIG. 2 illustrates a block diagram of exercise device components that can be used in connection with the present invention.

Exercise devices 12a-12c also include a processing unit (see FIG. 2). A processing unit can be a computer, a microprocessing unit, a microcontroller, state machine or other similar device that includes circuitry for controlling the operation of one or more features on an exercise device. For example, a processing unit on exercise device 12a may control the speed of belt 13a or inclination of deck 13b. A processing unit on exercise device 12b may control the actuators that adjust the resistance applied to flywheel 13c, or the inclination or stride length of foot rails 13d and/or arm rails 13e. A processing unit on exercise device 12c may control the actuators that adjust the resistance applied to flywheel 13f or the tilt of frame 13g. A processing unit may be located within the console of an exercise device or within another part of an exercise device. Alternatively, a processing unit may be external from the exercise device. A processing unit may include reference data, code, software, or other data or operating instructions for performing its function and executing commands. Reference data may include the limited range of operating parameters of a moveable member.

Exercise devices 12a-12c also include control consoles 26a-26c. Control consoles 26a-26c may include one or more interface devices. Interface devices may be either input devices or output devices. Input devices enable a user to manually input and vary the operating parameters of the moveable member on the exercise device. Examples of input devices include but are not limited to speed controls, incline controls, resistance controls, time controls, distance controls, a start button, a stop or pause button, and heart rate controls. These input devices may take the form of one or more buttons, switches, rheostats, potentiometers, touch sensitive controls, voice activated controllers, and the like.

In general, output devices provide information, either visually or audibly, to a person performing an exercise on exercise devices 12a-12c. This information, which can be referred to broadly as "motivational content," can include information regarding the exercise device. For example, an output device may provide information representative of the operating parameters of the exercise device, such as the speed, incline, resistance level, duration of workout, elevation climbed, etc. This information may be provided numerically, graphically, or through combinations thereof. To provide a more realistic experience, output devices may provide a representation of a trail, road, or path to be traversed by a person performing an exercise. Motivational content can also include information regarding the person exercising on the exercise device, such as biometric information. For example, an output device may provide information representative of the user's pulse, calories burned, blood pressure, etc.

Examples of output devices through which motivational content may be provided include but are not limited to speakers, video displays, liquid crystal display (LCD), light emitting diodes (LEDs), cathode ray tube (CRT) displays, electroluminescent displays (ELD), gas-plasma displays, thin film transistor (TFT) displays, virtual reality (VR) displays, and the like.

FIG. 2 illustrates a block diagram showing components that may be included in an exercise device 12, such as exercise devices 12a-c. For example, exercise device 12 may include a processing unit 50, a receiving port 52, an actuator 54, and a moveable member 13. Processing unit 50 is communicatively connected to the receiving port 52 and may be included within a console 26. Processing unit 50 is also communicatively connected to actuator 54. In response to control commands from processing unit 50, actuator 54 selectively adjusts one or more operating parameters of moveable member 13 within a limited range.

Data, including workout files, can be received by exercise device 12 through receiving port 52. As stated previously, workout files can include one or more control commands as well as motivational content. Control commands that provide control instructions to an exercise device (for example, a treadmill, elliptical machine, or exercise bike) may be referred to as a "control command subset." Thus, a control command subset may comprise a plurality of control commands that include, for example, control commands for a belt motor, an incline motor, and other actuators. In addition to actuator control commands, control command subsets may further include distance control commands and time control commands. These commands may provide a series of actuator control commands for execution at specific times or at specific distances. For example, a workout file may provide a control command for an actuator to be at a certain level for a specific amount of time or for a specific distance.

Using these control command subsets, processing unit 50 may control actuator 54 on an exercise device in the sequence and at the times or distances specified by the commands. For example, actuator control commands that provide a processing unit with commands for controlling a belt motor, incline motor, or other actuator may be included in a control command subset for exercise device 12a. Actuator control commands that provide a processing unit with commands for controlling a flywheel brake, incline motor, stride length motor, or other actuator may be included in a control command subset for exercise device 12b. Actuator control commands that provide a processing unit with commands for controlling a flywheel brake or other actuator may be included in a control command subset for exercise device 12c.

Actuator control commands can be received for different time segments or distance segments of an exercise program. For example, a ten minute exercise program may have twenty different control commands that provide a processing unit with a different command for controlling an actuator every thirty seconds. Alternatively, a ten mile exercise program may have twenty different control commands that provide a processing unit with a different command for controlling an actuator every half mile. Exercise programs may be of any duration or distance and different control commands may be received at any time or distance during the program.

These control command subsets may be executed by exercise device 12 or processing unit 50 in a number of different ways. For example, the control commands may be stored into a read/write memory that is included in processing unit 50. Alternatively, the control command subsets may be streamed to the exercise device. The control commands may also be received and/or executed from a portable memory device, such as a USB memory stick or an SD card.

Workout files, according to the present invention, may include a plurality of control command subsets that provide instructions for different types of exercise devices. For example, a workout file may include a first control command subset that includes control commands for controlling a belt motor and an incline motor on a treadmill. The workout file may also include a second control command subset that includes control commands for controlling a brake and a tilt motor on an exercise bike.

Workout files that include control command subsets that provide instruction for different types of exercise devices (e.g., treadmills, elliptical machines, exercise bikes) may be referred to herein as "universal workout files." When a universal workout file is received through receiving port 52 of an exercise device, the processing unit 50 recognizes the control command subset that is compatible with the actuators included on the exercise device. For example, reference data within processing unit 50 may be used to recognize the compatible control command subset. Once recognized, processing unit 50 may select the control command subset that is compatible with the actuators included on the exercise device. Processing unit 50 may ignore the control command subsets that are not compatible with actuators on the exercise device.

For example, a workout file that includes a control commands for controlling both the speed of a belt on a treadmill and the resistance applied to a flywheel on an exercise bike may be received by exercise device 12a and exercise device 12c. The processing unit within exercise device 12a recognizes and is able to select the control command subset that provides instructions for belt speed, while ignoring the control command subset that provides instructions for flywheel resistance. Similarly, the processing unit within exercise device 12c is able to select the control command subset that provides instructions for flywheel resistance, while ignoring the control command subset that provides instructions for belt speed.

In addition to recognizing and selecting the compatible control command subsets, processing unit 50 may also apply a sizing restriction to actuator control commands before the control commands can be executed by the exercise device. As with recognizing the compatible control command subsets, processing unit 50 may use reference data to determine whether a sizing restriction is necessary and, if so, apply the sizing restriction. Application of a sizing restriction to compatible control commands may be necessary due to the fact that the moveable members on exercise devices have operating parameters that are adjustable only within a limited range. Thus, even if two exercise devices have the same type of actuator (i.e., both have belt motors), a workout file that provides control commands for that actuator may not be compatible with both devices.

For example, a workout file may include an actuator control command that instructs a processing unit to set the speed of the belt motor on a treadmill to fifteen miles per hour. As long as fifteen miles per hour is within the operating parameters of the belt motor, the processing unit would be able execute this command. However, fifteen miles per hour is not within the operating parameters of all belt motors. Some belt motors may only achieve a belt speed of ten miles per hour, or less. To the extent a belt motor is not able to achieve a belt speed of fifteen miles per hour, processing unit 50 would apply a sizing restriction to the control commands such that the control commands after a sizing restriction has been applied fall within the limited range of operating parameters of the treadmill. Once processing unit 50 has applied a sizing restriction to a control command subset, the resized control command subset is referred to herein as a "restricted control command subset."

Figure 3A:
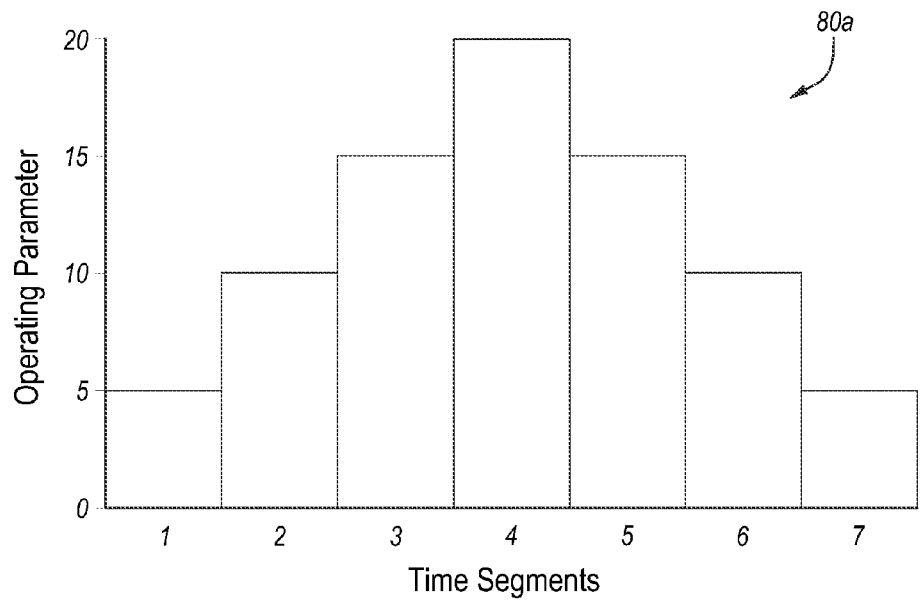
FIG. 3A illustrates graphically a profile of a workout file.
Figure 3B:
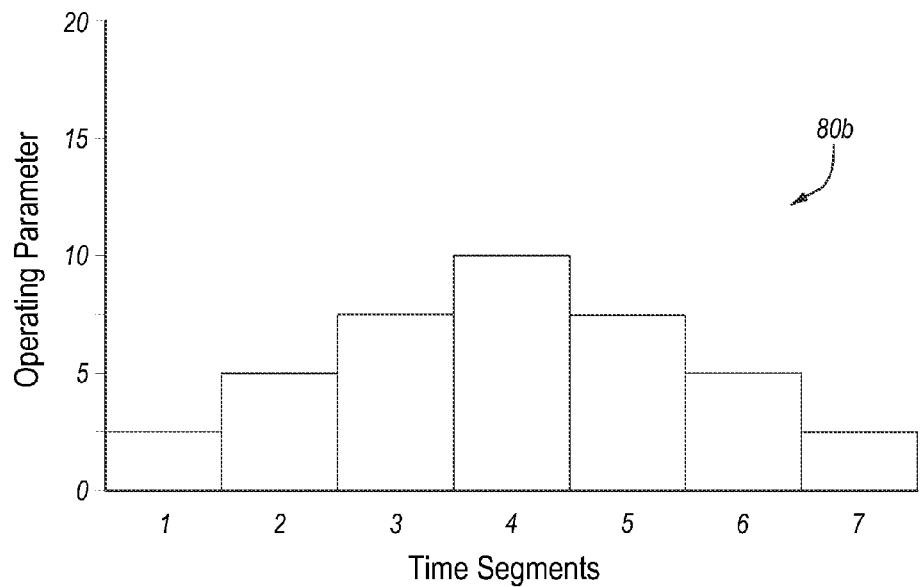
FIG. 3B illustrates graphically a profile of a workout file after application of a sizing restriction to the workout file.

Processing unit 50 can resize actuator control commands in different ways. For example, processing unit 50 may scale the size of the actuator control commands. FIG. 3A provides a graphical representation of a workout file profile 80*a*, with operating parameters on the y-axis and time segments in the x-axis. The operating parameters and time segments illustrated in FIG. 3A are representative of a series of timed control commands that may be included in a workout file. As can be seen in FIG. 3A, the highest operating parameter in workout file profile 80*a* is twenty. FIG. 3B illustrates workout file profile 80*a* of FIG. 3A after a scaling restriction has been applied by processing unit 50. As can be seen in FIG. 3B, each of the operating parameters has been reduced or scaled such that the highest operating parameter in the new workout file profile 80*b* is ten. In other words, to bring the highest operating parameter within the limited range, the highest operating parameter was reduced or scaled by fifty percent. In the present embodiment, all of the other operating parameters were also scaled by fifty percent.

With the sizing restriction applied, workout file profile 80*b* of FIG. 3B can now be executed by an exercise device that has a moveable member with an operating parameter limit of ten or less. This scaling adjustment may be performed by processing unit 50 automatically based on the limited range of operating parameters of the exercise device. Alternatively, this scaling adjustment may be performed by processing unit 50 based on user input.

Figure 4A:
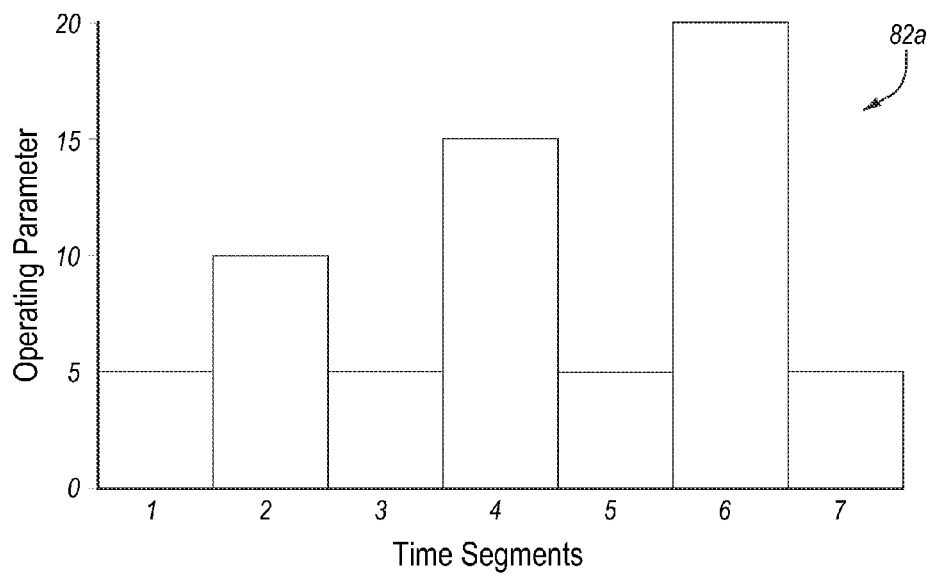
FIG. 4A illustrates graphically a profile of a workout file.
Figure 4B:
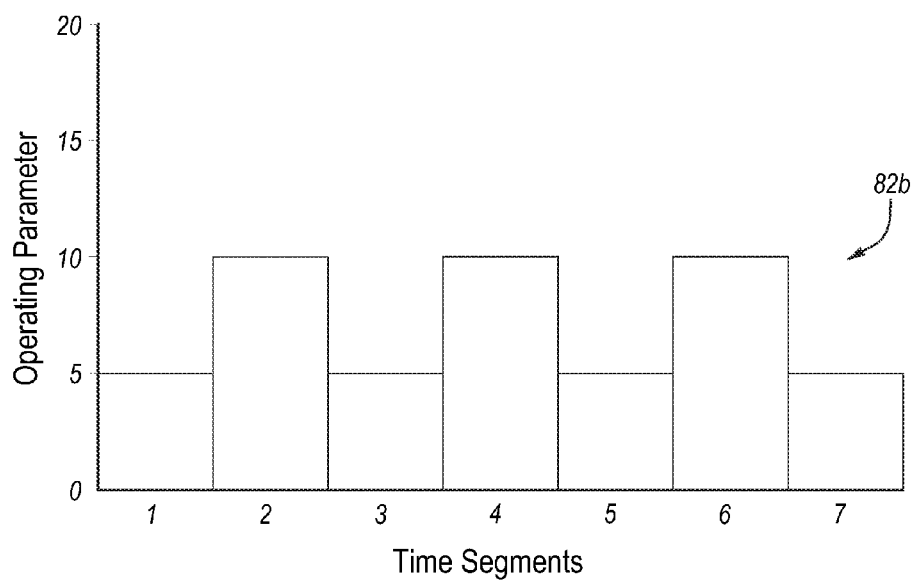
FIG. 4B illustrates graphically a profile of a workout file after application of a sizing restriction to the workout file.

Processing unit 50 may also resize actuator control commands by placing a cap on the size of actuator control commands. FIG. 4A provides a graphical representation of a workout file profile 82*a*, with operating parameters on the y-axis and time segments in the x-axis. As can be seen in FIG. 4A, exercise program 82*a* includes operating parameters of fifteen and twenty in time segments four and six, respectively. FIG. 4B illustrates workout file profile 82*a* of FIG. 4A after a capping restriction has been applied by processing unit 50. As can be seen in FIG. 4B, the highest operating parameter in the new workout file profile 82*b* is ten. That is, the operating parameter in time segments four and six were reduced down to ten each. As a result, workout file profile 82*a* has a maximum operating parameter level of ten. Workout file profile 82*b* of FIG. 4B can now be executed by an exercise device that has a moveable member with an operating parameter limit of ten or less. This capping adjustment may be applied by processing unit 50 to any control command that instructs actuator movement outside the limited range of operating parameters for a moveable member. This capping adjustment may be performed by processing unit 50 automatically based on the limited range of the operating parameters of the exercise device. Alternatively, this capping adjustment may be performed by processing unit 50 based on user input.

While a sizing restriction may be necessary due to the limited range of the operating parameters of a moveable member, sizing restrictions may also be performed in response to user input. For example, a user, using an input device, may scale actuator control commands in a workout file by a desired percentage. Referring back to FIGS. 3A and 3B, the actuator control commands of workout file profile 80*b* are fifty percent of the actuator control commands of workout file profile 80*a*. Thus, workout file profile 80*b* may be the result of a user's selection of fifty percent of original workout file profile 80*a*. Other percentages of the original workout file may be selected. For example, a user may want to scale the actuator control commands by seventy-five percent, ninety percent, etc. A user may also want to increase the actuator control commands of an original workout file by selecting, for example, one-hundred and ten percent or another percentage above one-hundred percent.

Figure 5A:
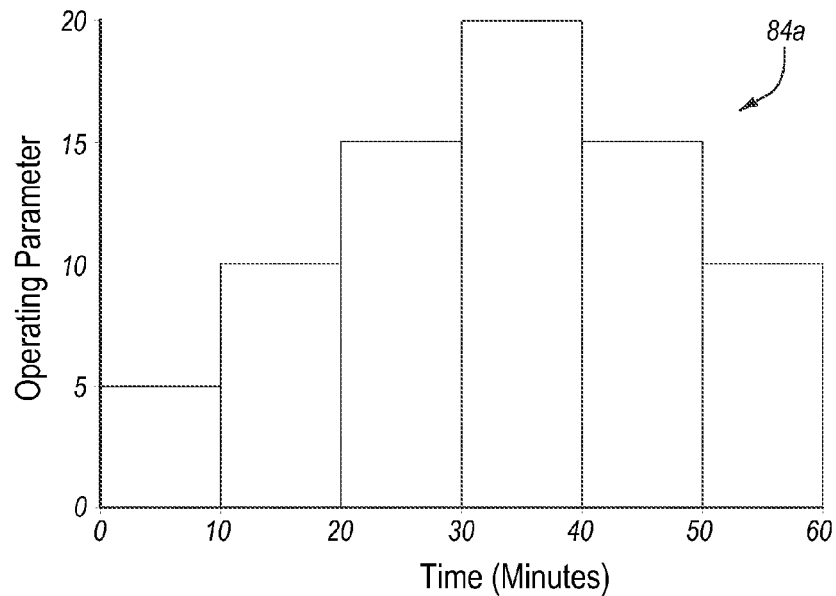
FIG. 5A illustrates graphically a profile of a workout file.
Figure 5B:
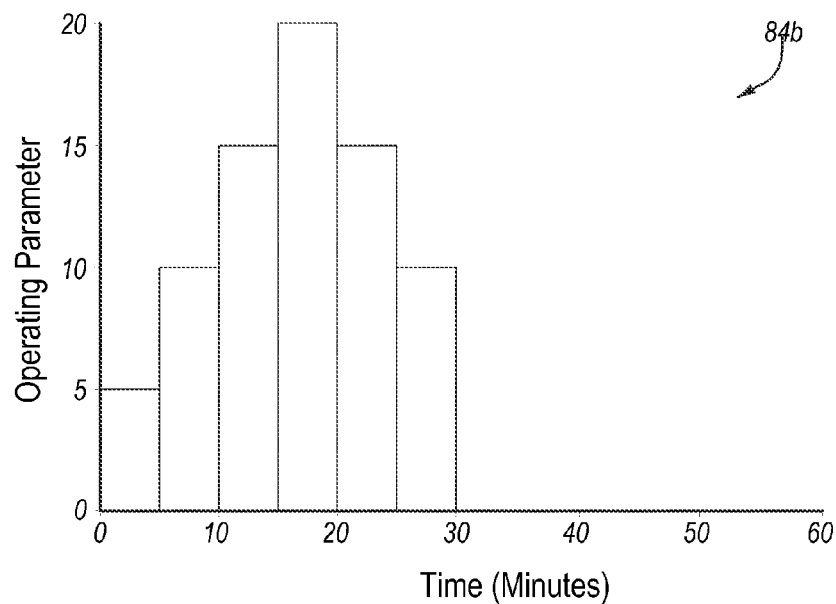
FIG. 5B illustrates graphically a profile of a workout file after application of a sizing restriction to the workout file.

In addition to size restrictions applied to actuator control commands, processing unit 50 may also modify or adjust the time commands associated with actuator control commands, to the extent time commands are included in the workout file. For example, FIG. 5A provides a graphical representation of workout file profile 84*a*, with actuator control commands on the y-axis and time, in minutes, in the x-axis. As can be seen in FIG. 5A, the total time duration for workout file profile 84*a* is sixty minutes. Different actuator control commands are provided at ten minute intervals creating six different time segments, each ten minutes long. FIG. 5B illustrates workout file profile 84*b* after a time restriction has been applied by processing unit 50. As can be seen in FIG. 5B, the total time duration for workout file profile 84*b* is thirty minutes. The duration of each of the six time segments has been reduced by fifty percent. Thus, instead of six time segments of ten minutes each as in workout file profile 84*a*, workout file profile 84*b* has six time segments of five minutes each. The time associated with an workout file profile may be modified based on user input. For example, the time modification reflected in FIGS. 5A and 5B may be the result of a user having input a desired workout time of thirty minutes.

Figure 6A:
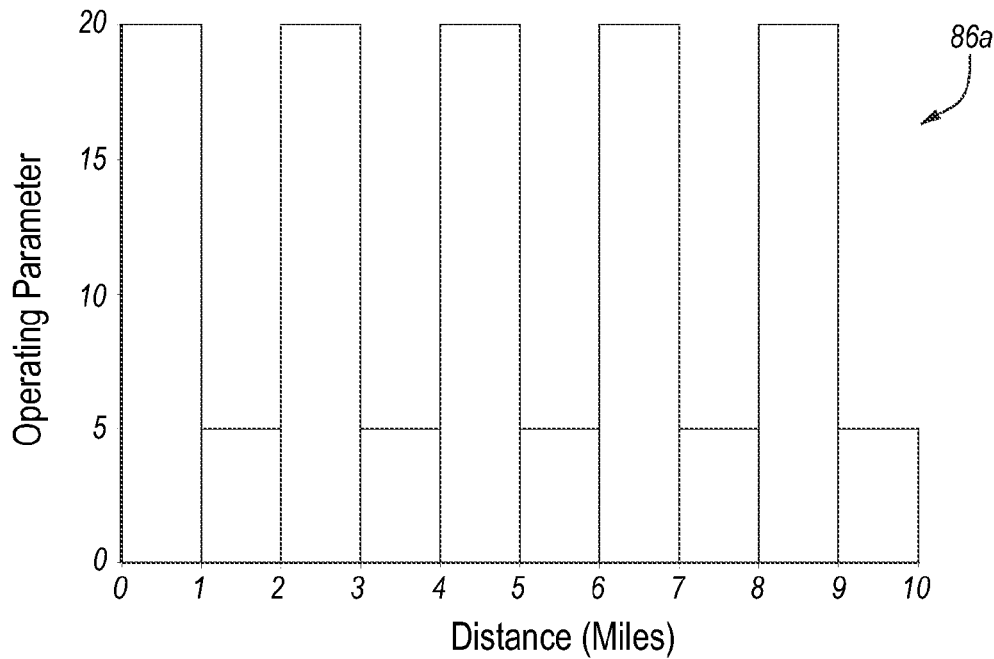
FIG. 6A illustrates graphically a profile of a workout file.
Figure 6B:
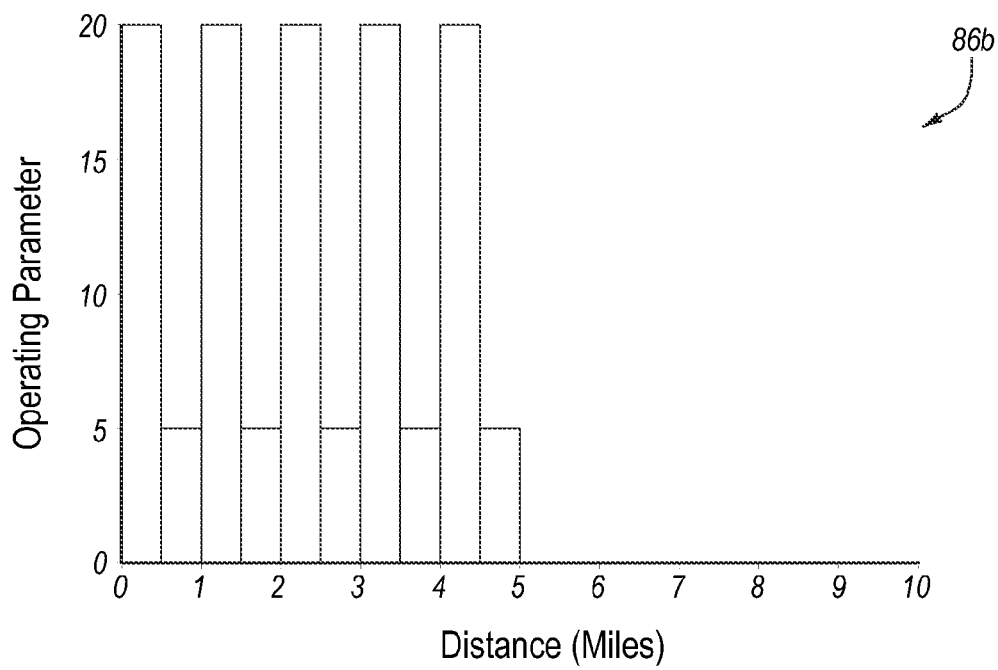
FIG. 6B illustrates graphically a profile of a workout file after application of a sizing restriction to the workout file.

Processing unit 50 may also modify or adjust the distance commands associated with actuator control commands, to the extent distance commands are included in the workout file. For example, FIG. 6A provides a graphical representation of an workout file profile 86*a*, with actuator control commands on the y-axis and distance, in miles, in the x-axis. As can be seen in FIG. 6A, the total distance of workout file profile 86*a* is ten miles. Different actuator control commands are provided at one mile intervals creating ten different distance segments. FIG. 6B illustrates workout file profile 86*b* after a distance restriction has been applied by processing unit 50. As can be seen in FIG. 6B, the total distance of workout file profile 86*b* is five miles. The distance of each of the ten distance segments has been reduced by fifty percent. Thus, instead of ten distance segments of one mile each as in workout file profile 86*a*, workout file profile 86*b* has ten distance segments of one-half mile each. The distance associated with an workout file profile may be modified based on user input. For example, the distance modification reflected in FIGS. 6A and 6B may be the result of a user having input a desired workout distance of five miles.

Workout files may also include motivational content. The motivational content may be synchronized with or reflective of the control commands within a workout file. For example, motivational content may include a video of terrain to be traversed that is displayed to a user. This video may be synchronized with control commands such that the control commands correspond to what is shown on the video. This may be accomplished by adjusting the horizon line on the video as an incline motor changes the incline on an exercise device. This may also be accomplished by increasing the rate at which the video is played back as a belt motor changes the speed of a belt on an exercise device.

Motivational content may also include a graphical representation of a workout file profile, such as those that are illustrated in FIGS. 3A-6B. This graphical representation of a workout file profile may be reflective of the control commands in the workout file such that the workout file profile shows the sequence of operating parameter adjustments in the workout.

Motivational content may further include projected biological metrics. These biological metrics may include but are not limited to caloric expenditure, metabolic equivalent of task, and carbohydrate expenditure. Biological metrics may be reflective of the control commands and the actual biological metrics that are anticipated for a person that performs and exercise that implements the control commands.

Processing unit 50 may adjust, alter, or otherwise modify the motivational content that is included in a workout file. Motivational content that has been modified by processing unit 50 is referred to herein as "modified motivational content." Motivational content may be modified by processing unit 50 in connection with or independently from modifications made to actuator control commands, time control commands, or distance control commands. Motivational content may be modified by processing unit 50 so that the modified motivational content remains synchronized with or reflective of a restricted control command subset.

Figure 7A:
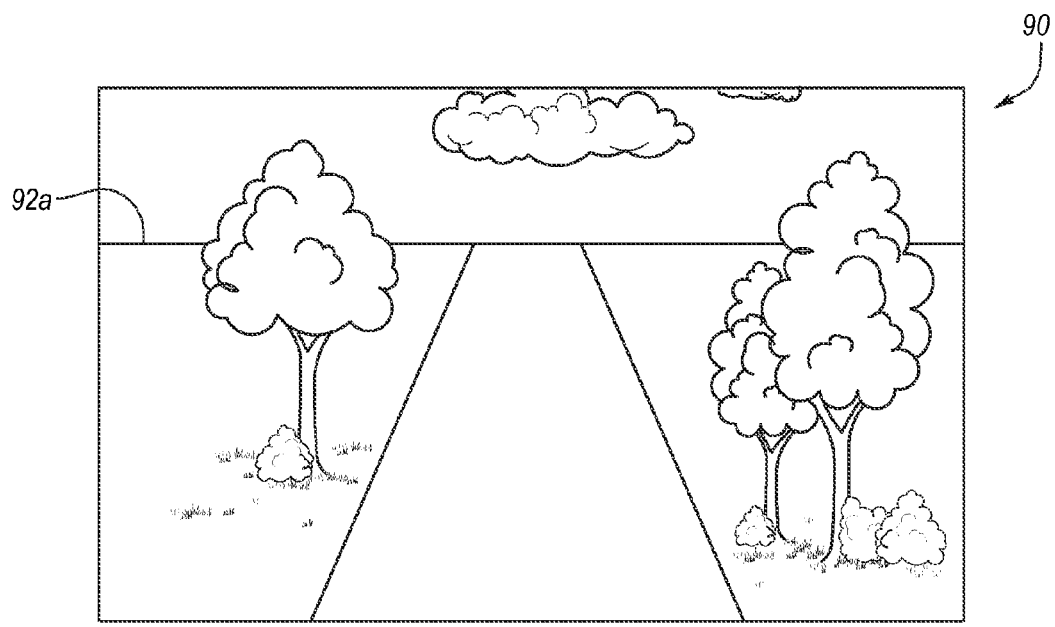
FIG. 7A illustrates a frame from a video showing terrain to be traversed by the user during performance of an exercise.
Figure 7B:
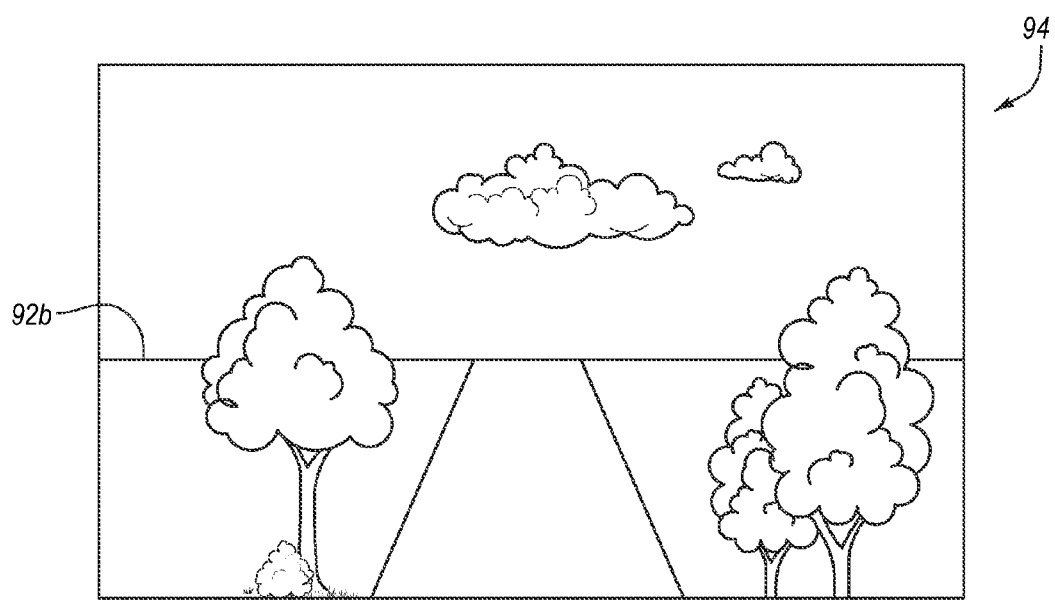
FIG. 7B illustrates a frame from a video showing terrain to be traversed by the user during performance of an exercise after an adjustment to the horizon line.

For example, an adjustment to a control command in a workout file may cause an adjustment to a video of terrain to be traversed that is displayed to the user. FIG. 7A illustrates a frame 90 from a video showing terrain to be traversed by the user during performance of an exercise. Frame 90 includes a horizon line 92*a*. Frame 90 illustrated in FIG. 7A may be shown on a display incorporated on the console of an exercise device or in another location. FIG. 7B illustrates a frame 94 from the video showing terrain to be traversed by the user during performance of an exercise after an adjustment to the horizon line on the video. As can be seen, the horizon line 92*a* shown in FIG. 7A is higher than the horizon line shown 92*b* in FIG. 7B. Processing unit 50 may modify the horizon line position so that the horizon line in a video remains synchronized with the inclination executed by the actuators of an exercise device. For example, the horizon line adjustment shown in FIGS. 7A and 7B can be made in connection with a modification to control commands which decreases the inclination implemented on a treadmill or elliptical machine.

In addition, if actuator control commands for a belt motor on a treadmill are modified, the playback speed of the video could be modified so that the video is played at a rate that corresponds with the speed that the belt is rotating. For example, if processing unit 50 cuts actuator control commands for a belt motor in half, processing unit 50 may also double the playback speed of a video so that the video remains synchronized with the restricted control command subset.

An adjustment to actuator control commands in a workout file may also cause an adjustment to a graphical representation of a workout file profile. For example, if processing unit 50 modifies control commands in a workout file, processing unit 50 may also modify a graphical representation of the workout file profile so that the workout file profile remains reflective of the restricted control command subset.

Further, an adjustment to actuator control commands in a workout file may also cause an adjustment to projected metrics for a user performing the exercise. For example, if control commands in a workout file are modified, processing unit 50 may also modify the projected metrics so that the projected metrics reflect the restricted control command subset.

Finally, in addition to motivational content, other control commands may be adjusted in response to adjustments to actuator control commands. For example, a workout file may include instructions for fan speed. If actuator control commands for the belt speed on a treadmill are modified, processing unit 50 may also modify control commands for the speed of a fan may so that the fan speed remains reflective of the belt speed, thus creating a more realistic workout experience for a user.

Figure 8:
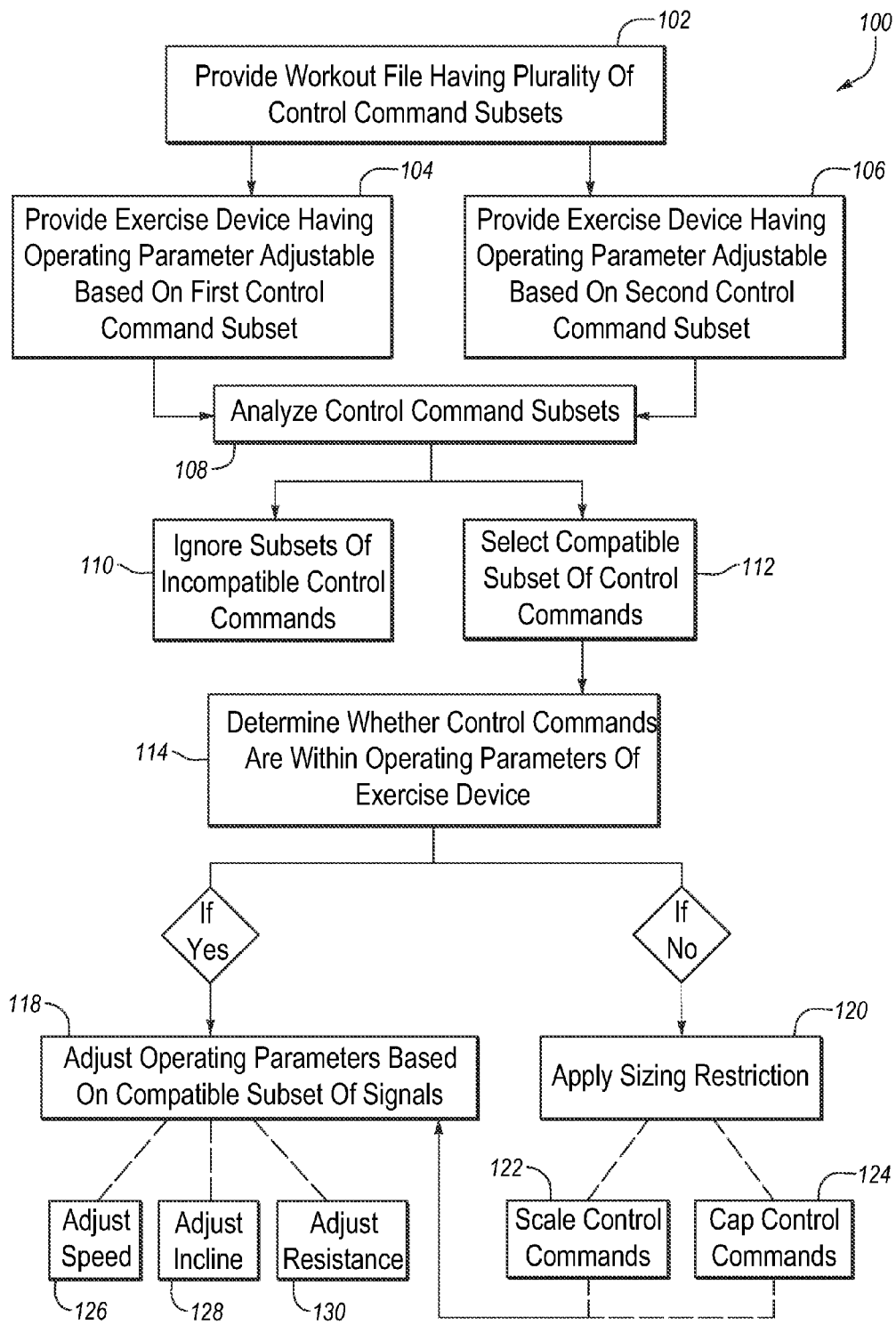
FIG. 8 illustrates steps that may be implemented in a method for controlling an exercise device.

The present invention also includes a method 100 for controlling an exercise device. FIG. 8 illustrates steps that may be implemented in method 100 for controlling an exercise device. In a first step 102, a workout file having a plurality of control command subsets, including a first subset of control commands and a second subset of control commands, is provided. In step 104, a first exercise device having at least one moveable member that is selectively adjustable within a limited range and that is adjustable based on the first subset of control commands is provided. The method of the present invention may be limited to a single exercise device. However, a method for controlling multiple exercise devices is disclosed. For example, method 100 includes steps for controlling a second exercise device. In step 106, a second exercise device having at least one moveable member that is selectively adjustable within a limited range and that is adjustable based on the second subset of control commands is provided.

In step 108, the first and second exercise devices each analyze the control command subsets included in the workout file. Control commands that are incompatible with each exercise device are ignored in step 110, while the compatible subset of control commands is selected in step 112. For example, if the first exercise device is a treadmill, the processing unit of the treadmill would ignore control command subsets for a flywheel brake and would select the control command subset for belt speed. If the second exercise device is an exercise bike, the processing unit of the exercise bike would ignore control command subset for belt speed and would select the control command subset for a flywheel brake.

In step 114, the first and second exercise devices each determine whether the selected control commands are within the limited range of the operating parameters of each machine's respective moveable members. If the selected control commands are within the operating parameters of each machine's respective moveable members, then each exercise device adjusts the operating parameters based on the compatible and selected subset of control commands in step 118.

Alternatively, if one or more control commands are outside the limited range of the operating parameter of the machine's moveable member, then a sizing restriction is applied in step 120. Sizing restrictions can be based on a scaling function (step 122) or a capping function (step 124), as those restrictions have been described hereinabove. Alternatively, a different sizing restriction could be applied to reduce the size of at least the control commands that are outside the operating parameter ranges of the exercise devices. Once a sizing restriction has been applied, then the exercise device adjusts the operating parameters based on the compatible subset of control commands in step 118.

FIG. 9 illustrates tables that include components of the present invention. For example, FIG. 9 illustrates a table 150, which identifies data that may be included in a workout file. The workout file illustrated in table 150 includes control commands that provide instructions for controlling the actuators 152 that selectively adjust the operating parameters of multiple moveable members during different time segments 154, 156, 158. More specifically, the workout file illustrated in table 150 includes control commands that provide instructions for controlling a belt motor, an incline motor, a brake, a stride length motor, and a tilt motor. Because these actuators correspond to different exercise devices, the workout file illustrated in table 150 is a universal workout file. A workout file may include instructions for controlling actuators in addition to or fewer than those explicitly identified in table 150.

The workout file illustrated in table 150 also includes three time segments 154, 156, and 158. Control commands for each of the actuators are provided for each of the time segments 154, 156, 158. Specifically, with regard to the belt motor, a control command of six is provided for time segment one 154, a control command of ten is provided for time segment two 156, and a control command of twenty is provided for time segment three 158. These control commands may represent a speed in miles per hour or another unit. Control commands are also provided for each time segment for the incline motor, brake, stride length motor, and tilt motor. The control commands for the incline motor may represent an angle, for example, degrees from horizontal. The control commands for the brake may represent a frictional resistance in Newtons or another unit. The control commands for the stride length motor may represent a distance or length in inches or another unit. The control commands for the tilt motor may represent an angle, for example, degrees from vertical. Workout file 150 may include time segments in addition to or fewer than those explicitly identified.

FIG. 9 also illustrates tables (160, 170, 180), which include control command subsets taken from the workout file in table 150. Specifically, table 160 includes a control command subset for a treadmill 164. For example, the control command subset illustrated in table 160 includes control commands from the workout file in table 150 that provide instructions for controlling a belt motor and an incline motor. Table 160 also includes reference data 162 that identifies the limited range of operating parameters for the actuators on treadmill 164. For instance, in the illustrated embodiment the belt motor has a range of operating parameters of zero to ten miles per hour and the incline motor has a range of operating parameters of zero to fifteen degrees/% grade. As can be seen, the workout file notably includes a belt motor control command of 20 miles per hour, which is outside the belt motor's range of operating parameters and which will be discussed in greater detail below.

Table 170 includes a control command subset for an elliptical machine 174. For example, the control command subset illustrated in table 170 includes control commands from the workout file in table 150 that provide instructions for controlling an incline motor, a brake, and a stride length motor. Table 170 also includes reference data 172 that identifies the limited range of operating parameters for the actuators on elliptical machine 174. Specifically, the incline motor has a range of operating parameters of zero to ten degrees and the brake has a range of operating parameters of zero to ten Newtons. The stride length motor has a range of operating parameters of zero to five inches. As can be seen, the workout file includes a brake control command of 20, which is outside the brake's operating parameter range of zero to ten Newtons.

Table 180 includes a control command subset for an exercise bike 184. For example, the control command subset illustrated in table 180 includes control commands from the workout file in table 150 that provide instructions for controlling a brake and a tilt motor. Table 180 also includes reference data 182 that identifies the limited range of operating parameters for the actuators on exercise bike 184. Specifically, the brake has a range of operating parameters of zero to twenty Newtons. The tilt motor has a range of operating parameters of zero to five degrees. As can be seen, the workout file includes a tilt motor control command of 10, which is outside the tilt motor's operating parameter range of zero to five degrees.

FIG. 9 also illustrates tables (190, 192, 200, 202, 210, 212), which include restricted control command subsets. Specifically, table 190 illustrates the control command subset of table 160 after application of a capping sizing restriction. As can be seen in table 190, the belt motor control commands have been capped such that each control command is within the belt motor's range of operating parameters. Table 192 illustrates the control command subset of table 160 after application of a scaling sizing restriction. Table 192 identifies the scaling factors that are applied to the belt motor control commands. These scaling factors may be stored in the processor of the exercise device or could be calculated by the processor based on the control commands included in the workout file and the reference data. Scaling factors applied to control commands for each actuator may be the same or different. As can be seen in table 192, after application of the scaling factors, each belt motor control command is within the belt motor's range of operating parameters.

Table 200 illustrates the control command subset of table 170 after application of a capping sizing restriction. As can be seen in table 200, the brake control commands have been capped such that each control command is within the brake's range of operating parameters. Table 202 illustrates the control command subset of table 170 after application of a scaling sizing restriction. Table 192 identifies the scaling factors that are applied to the brake control commands. As can be seen in table 192, after application of the scaling factors, each brake control command is within the brake's range of operating parameters.

Table 210 illustrates the control command subset of table 180 after application of a capping sizing restriction. As can be seen in table 210, the tilt motor control commands have been capped such that each control command is within the tilt motor's range of operating parameters. Table 212 illustrates the control command subset of table 180 after application of a scaling sizing restriction. Table 192 identifies the scaling factors that are applied to the tilt motor control commands. As can be seen in table 192, after application of the scaling factors, each tilt motor control command is within the tilt motor's range of operating parameters.

INDUSTRIAL APPLICABILITY

In general, the present invention relates to workout files that include control commands for controlling the actuators on a plurality of different exercise devices. Exercise devices of the present invention are able to receive, recognize, select, resize (if necessary) and execute compatible control commands while ignoring incompatible control commands. Exercise devices that are able to recognize and select compatible control command subsets allow a single universal workout file to be used by a variety of different exercise devices. This eliminates the need for consumers to obtain workout files that are uniquely designed for their type of exercise device. For example, a "Fat Burn" workout file could be stored onto a single SD card and be executed by a treadmill, elliptical machine, exercise bike, and other exercise devices.

While the invention has been described in the context of motorized treadmills, stationary exercise cycles, and elliptical machines, one of skill in the art will understand that the invention is not limited to any particular type of exercise device. To the contrary, the present invention can be readily adapted to any motorized device or any other device that utilizes motors, solenoids, or any other electrically driven actuators to control any operating parameter of a moveable member on an exercise device. For example, exercise devices may include treadmills, exercise bikes, Nordic style skiers, rowers, steppers, hikers, climbers, elliptical machines, and striding exercise machines. Operating parameters may include but are not limited to belt speed, resistance, incline, stride length or other similar operating parameter. A moveable member can be any part of an exercise device that moves during the performance of an exercise on that device. An actuator may be any device that selectively adjusts the operating parameters of a moveable member within the limited range.

Exercise devices of the present invention may obtain a workout file through one or more receiving ports. Exercise devices of the present invention may receive these workout files through the receiving ports and from any remote source, including but not limited to portable storage devices or from a remote communication system. The workout file may include only control commands. Alternatively, the workout file may contain both control commands and motivational content.

Control command subsets in the workout file may provide instructions to exercise device processing units for controlling actuators (for example, a belt motor). Workout files of the present invention may include a plurality of control command subsets. For example, a workout file may include a control command subset for controlling a belt motor, as well as other control command subsets for controlling an incline motor, a flywheel brake, and other actuators found on exercise devices.

Exercise devices of the present invention may include processing units that identify the control command subsets that provide instructions for controlling the actuators of the exercise device. Processing units may ignore control command subsets that provide instructions for controlling actuators that are not a part of the exercise device. For example, a treadmill processing unit may identify or recognize a control command subset that provides instructions for controlling a belt motor while ignoring control command subsets for controlling a flywheel brake. Processing units may include reference data or other software for identifying the relevant control command subset(s).

Once a processing unit has identified the relevant control command subsets within a workout file, the processing unit analyzes the control commands within the subset. The processing unit determines whether the control commands provide instructions for controlling the actuator within the limited range of the operating parameters of the moveable member. For example, a treadmill may include a belt motor that is only able to achieve a belt speed of up to ten miles per hour. Thus, the operating parameters of the belt have a limited range of zero to ten miles per hour within which it may be selectively adjusted by a belt motor.

To the extent that the processing unit determines that there is a control command that provides instructions for controlling an actuator outside of the limited range of the moveable member's operating parameters, the processing unit applies a sizing restriction to the control command(s), thereby creating a restricted control command subset. The processing unit may apply a sizing restriction to just the control command(s) that are outside of the limited range of moveable member's operating parameters. For example, the processing unit may simply cap the control command(s) that are outside of the limited range of operating parameters. For example, if a treadmill includes a belt motor that is only able to achieve a belt speed of ten miles per hour, any control command within the workout file may be capped at ten miles per hour.

Alternatively, the processing unit may apply a sizing restriction that scales all of the control commands within a workout file such that each of the control command provide instructions for controlling an actuator within the limited range of operating parameters of the moveable member. For example, if a treadmill includes a belt motor that is only able to achieve a belt speed of ten miles per hour and a control command provides instruction for setting the belt motor to twenty miles per hour, the processing unit may scale all of the control commands within the subset by fifty percent.

To the extent that the processing unit applies a sizing restriction to one or more control commands, the processing unit may also modify motivational content included in a workout file, thereby creating modified motivational content. For example, if a video of terrain to be traversed by a user is included in a workout file, the playback speed of that video or the horizon line may be modified when a sizing restriction is applied to a control command. Modifying the motivational content may be necessary so that the motivational content remains synchronized with or accurate with the restricted control command subset.

Other motivational content may be modified as well. For example, the timing of audible encouragement may be altered so that it is provided at a specific part of a workout (for example, just prior to a particularly intense part of a workout), a visual display of a workout profile, projected biological metrics, etc. In addition, other data or control commands within a workout file may also be modified. For example, fan speed may be modified to correspond to a restricted control command subset.

The invention claimed is:
1. A first exercise device comprising:
a first moveable member having one or more operating parameters selectively adjustable within a range;
one or more actuators that selectively adjust the one or more operating parameters within the range;
a receiving port that receives a workout file, the workout file comprises a first actuator control command subset that provides instructions to selectively adjust the one or more operating parameters of the first moveable member within the range and a second actuator control command subset to control a second moveable member of a different type of exercise device, where the second actuator control command subset is incompatible with the one or more operating parameters of the first moveable member;
a processing unit that is in communication with the one or more actuators and the receiving port, the processing unit including reference data that enables the processing unit to select the first actuator control command subset from the workout file;
wherein the processing unit further uses the reference data to analyze the first actuator control command subset and automatically apply a sizing restriction to the first actuator control command subset to create a restricted actuator control command subset when one or more of the control commands in the first actuator control command subset are outside the range of the one or more operating parameters of the first movable member.
2. The first exercise device of claim 1, wherein the workout file further comprises motivational content.

3. The first exercise device of claim 2, wherein the motivational content is synchronized with or reflective of the control commands within the workout file.

4. The first exercise device of claim 3, wherein the reference data enables the processing unit to modify the motivational content.

5. The first exercise device of claim 4, wherein the motivational content includes a video of terrain to be traversed during performance of an exercise and wherein the processing unit modifies a horizon line on the video so that the horizon line on the video remains synchronized with the restricted actuator control command subset.

6. The first exercise device of claim 4, wherein the motivational content includes a video of terrain to be traversed during performance of an exercise and wherein the processing unit modifies a playback speed of the video so that the playback speed of the video remains synchronized with the restricted actuator control command subset.

7. The first exercise device of claim 4, wherein the motivational content includes a graphical representation of a workout file profile and wherein the processing unit modifies the graphical representation of the workout file profile so that the workout file profile remains reflective of the restricted actuator control command subset.

8. The first exercise device of claim 4, wherein the motivational content includes projected biological metrics and wherein the processing unit modifies the projected biological metrics so that the projected biological metrics remain reflective of the restricted actuator control command subset.

9. The first exercise device of claim 1, wherein the workout file is a universal workout file and includes control command subsets for at least two different types of exercise devices.

10. The first exercise device of claim 9, wherein the two different types of exercise devices are selected from the group consisting of treadmills, elliptical machines, and exercise bikes.

11. The first exercise device of claim 1, wherein the sizing restriction applied by the processing unit is a scaling sizing restriction.

12. The first exercise device of claim 1, wherein the sizing restriction applied by the processing unit is a capping sizing restriction.

13. The first exercise device of claim 1, wherein the restricted actuator control command subset may be modified based on a user input.

14. The first exercise device of claim 1, wherein the receiving port is a memory device drive.

15. An exercise system comprising:
a remote computer that provides at least one workout file, w that includes a first subset of actuator control commands and a second subset of actuator control commands;
a first exercise device having a first processing unit and one or more operating parameters that are selectively adjustable within a range, wherein the one or more selectively adjustable operating parameters are adjustable within the range based on the first subset of actuator control commands from the at least one workout file, and wherein the first processing unit includes reference data that allows the first exercise device to identify and execute the first subset of actuator control commands; and
a second exercise device having a second processing unit and one or more operating parameters that are selectively adjustable within a range, wherein the one or more selectively adjustable operating parameters of the second exercise device are adjustable within the range based on the second subset of actuator control commands from the at least one workout file, and wherein the second processing unit includes reference data that allows the second exercise device to identify and execute the second subset of control commands;
wherein the first subset of the actuator control commands is incompatible with the second exercise device and the second subset of the actuator control commands is incompatible with the first exercise device; and
wherein the first processing unit automatically applies a sizing restriction to the first subset of the actuator control commands to create a restricted subset of the actuator control commands when at least one of the control commands in the first subset of the actuator control commands are outside the range of the one or more operating parameters of the first exercise device.

16. A method for controlling one or more exercise devices, the method comprising:
providing a workout file having a plurality of actuator control command subsets, including a first subset of the actuator control commands and a second subset of the actuator control commands;
providing a first exercise device having a processing unit and a first movable member having one or more operating parameters that is selectively adjustable within a range and that is adjustable based on the first subset of the actuator control commands and where the second subset of the actuator control commands is incompatible with the first exercise device;
selecting, with the processing unit, the first subset of actuator control commands from the plurality of the actuator control command subsets;
automatically applying, by the processing unit, a sizing restriction to the first subset of the actuator control commands to create a restricted subset of the actuator control commands when at least one of the control commands in the first subset of the actuator control commands are outside the range of one or more operating parameters of the first movable member; and
adjusting, by the processing unit, the one or more operating parameters of the first movable member based on the restricted subset of the actuator control commands.

17. The method of claim 16, further comprising:
providing a second exercise device having a processing unit and a second moveable member having one or more operating parameters that is selectively adjustable within a range; and
adjusting the one or more operating parameters of the second moveable member based on the second subset of actuator control commands.

* * * * *